United States Patent [19]

Wendell et al.

[11] Patent Number: 5,344,412
[45] Date of Patent: Sep. 6, 1994

[54] MICROBORE CATHETER WITH SIDE PORT(S)

[75] Inventors: Amy M. Wendell, Franklin; James R. Gross, Wareham; James P. Cianci, Walpole, all of Mass.

[73] Assignee: The Kendall Company, Mansfield, Mass.

[21] Appl. No.: 24,024

[22] Filed: Mar. 1, 1993

Related U.S. Application Data

[63] Continuation of Ser. No. 804,574, Dec. 10, 1991.

[51] Int. Cl.⁵ .................. B23K 26/00; A61M 5/00
[52] U.S. Cl. ..................... 604/280; 219/121.71
[58] Field of Search ............... 604/280; 264/25, 154; 219/121.71, 121.70

[56] References Cited

U.S. PATENT DOCUMENTS

| | | | |
|---|---|---|---|
| 4,028,525 | 6/1977 | Mominee et al. | 264/25 |
| 4,100,393 | 7/1978 | Luther | 219/121.71 |
| 4,478,677 | 10/1984 | Chen et al. | 219/121.71 |
| 4,948,941 | 8/1990 | Altman et al. | 219/121.71 |
| 4,961,731 | 10/1990 | Bodicky et al. | 604/280 |
| 4,968,307 | 11/1990 | Dake et al. | 604/280 |
| 4,973,321 | 11/1990 | Michelson | 604/280 |
| 5,021,044 | 6/1991 | Sharkawy | 604/280 |
| 5,026,965 | 6/1991 | Ohe et al. | 219/121.71 |
| 5,066,357 | 11/1991 | Smyth, Jr. et al. | 219/121.71 |
| 5,087,396 | 2/1992 | Zablotny et al. | 219/121.71 |
| 5,141,499 | 8/1992 | Zappacosta | 604/280 |

Primary Examiner—Paul J. Hirsch
Attorney, Agent, or Firm—Alvin Isaacs

[57] ABSTRACT

Disclosed are microbore catheters for spinal anesthesia having one or more side ports provided by a laser beam.

3 Claims, 1 Drawing Sheet

MICROBORE CATHETER WITH SIDE PORT(S)

This is a continuation division of application Ser. No. 07/804,574, filed Dec. 10, 1991.

BACKGROUND OF THE INVENTION

Catheters with side ports are per se well known in the art. For instance, epidural catheters currently commercially available from Kendall Healthcare Company, a division of The Kendall Company, assignee of the present invention, include side holes or ports in order to provide better drug dispersion than that obtained from a single opening at the distal end of the catheter lumen. Such side ports are produced by mechanical methods, e.g. skiving with a sharp instrument or drilling with a small bit.

While entirely satisfactory for epidural catheters (or larger ones), the known mechanical procedures are not applicable for so-called microbore or small bore catheters, i.e. catheters no greater than 24 gauge (outer diameter=0.022 in). For example, the preferred microbore catheters contemplated by the present invention are almost two times smaller than the typical 20 gauge epidural catheter:

| EPIDURAL (20 gauge) | MICROBORE SPINAL (28 gauge) |
| --- | --- |
| OD 0.036 in | OD 0.014 in |
| ID 0.020 in | ID 0.007 in |

OD = outer diameter
ID = inner diameter

By way of further explanation, the epidural catheter's side port diameter is typically on the order of 0.011 inch or on the order of fifty-five percent (55%) of the catheter's ID.

As is recognized in the art, the tendency for a patient to have rather severe headaches following spinal anesthesia is markedly reduced if a smaller needle is used. This in turn means that in conventional systems where the catheter is introduced through the needle, a smaller bore catheter is also required.

While for this reason microbore catheters are greatly preferred, if also desired that the microbore spinal catheter, like the larger epidural catheter have one or more side ports along with its distal end port to insure proper drug dispersion within the subarachnoid space. In the light of the state of the art at the time the present invention was made, these two characteristics appeared to be mutually exclusive so that one must either elect to have a microbore catheter without side ports or to have a larger bore catheter with side ports.

Stated simply, the task of the present invention was to devise a way to have the desired side port(s) in a microbore catheter.

BRIEF DESCRIPTION OF THE INVENTION

In accordance with the present invention this task is solved simply and elegantly by producing the side ports having the desired properties with a laser to be described in more detail hereinafter.

DETAILED DESCRIPTION OF THE INVENTION

Figure 1:
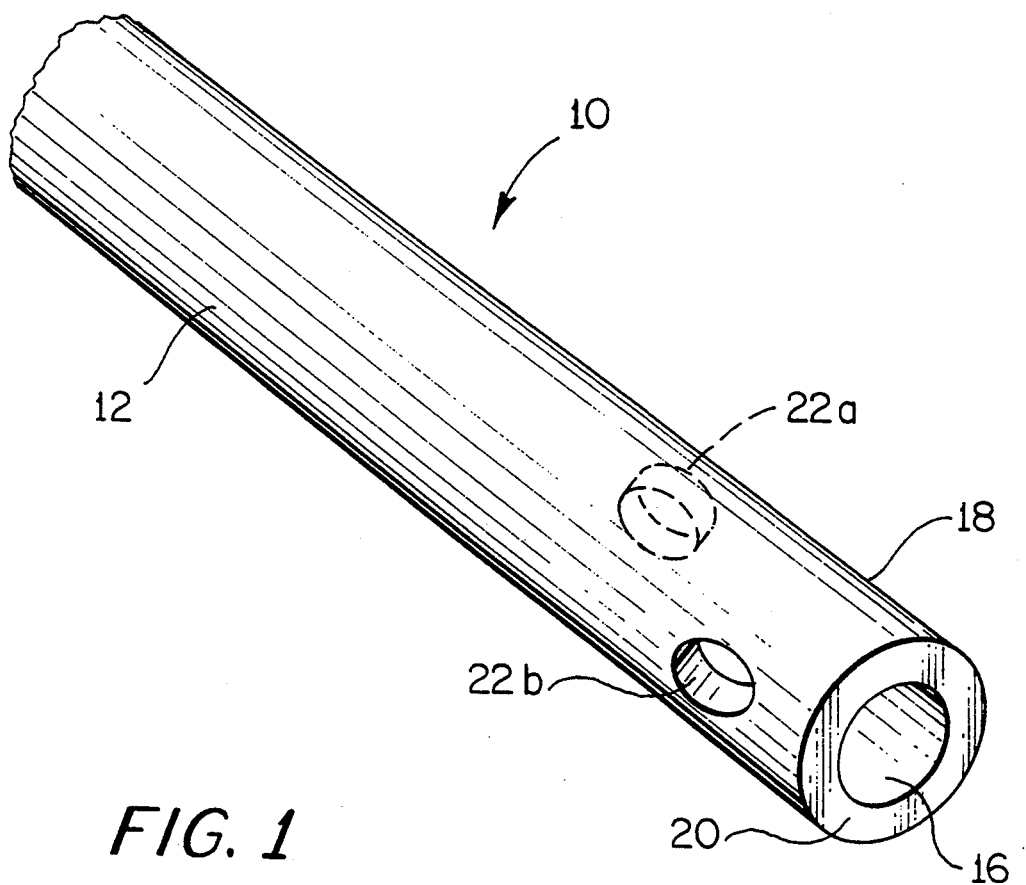
FIG. 1 is a fragmented perspective view, greatly enlarged of the distal portion of a novel catheter of this invention having two side ports.
Figure 2:
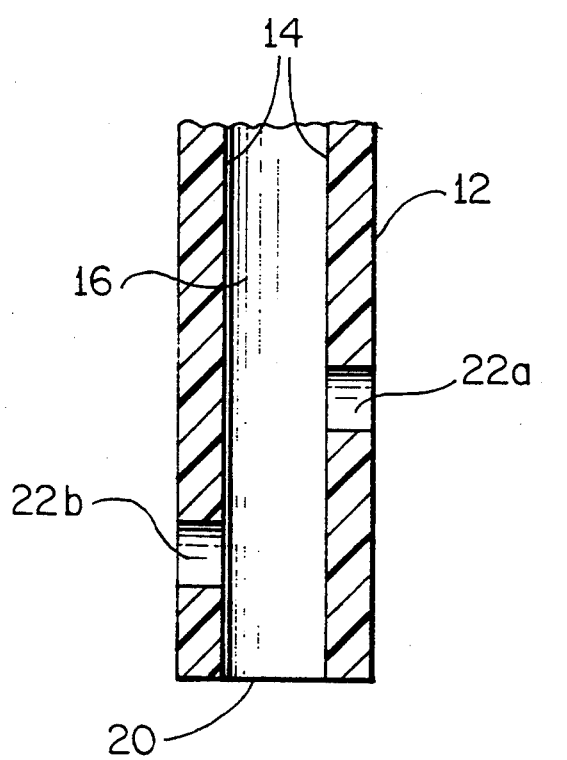
FIG. 2 is a longitudinal sectional view of the novel microbore catheter as shown in FIG. 1.

As heretofore mentioned, the present invention is directed to microbore catheters having particular utility in administering spinal anesthesia wherein the catheter has at least one side port or opening in addition to the opening at the distal end of the catheter. Catheters of this description provide improved drug dispersion over that which may be obtained with catheters having a single opening at the terminal end of the lumen in fluid communication with the drug source.

A preferred form of a catheter of this general description is shown in the illustrative drawings.

As shown therein, catheter 10 greatly enlarged for purposes of illustration) has inner and outer walls 14 and 12, respectively defining a lumen 16 extending from its proximal or trailing end (not shown), where it can be placed in fluid communication with a source of liquid drug, to its distal or leading end 18 terminating in opening 20 for drug administration, e.g. within the subarachnoid space. In accordance with this invention, catheter 10 is shown to have two additional openings 22a and 22b on opposed sides near the distal end 18.

In order to maximize drug distribution while not adversely decreasing tensile strength, ports 22a and b are not opposite one another but instead are offset longitudinally with port 22a proximal to port 22b. Since for administering spinal anesthesia the catheter is generally inserted no more than 2 cm within the subarachnoid space, it will be appreciated that port 22a should be no further than about 1.5 cm from the distal end 18, and preferably on the order of about 1.0 cm. Port 22b may be on the order of 0.5 cm from distal end 18.

Preferably, the size of ports 22a and 22b should be on the order of a 1:1 ratio with the catheter wall thickness. For instance, with a 28 gauge catheter as mentioned above, the wall thickness is the difference between the OD and ID of about 0.0007 in. divided by two or 0.0035 in. Accordingly, for a 28 gauge catheter the hole size should preferably be on the order of 0.0035 in ±0.001 inch in tolerance.

While the ports are shown to be generally spherical, the shape is not critical and other shape holes which can be provided to the microbore catheter are equally applicable.

In the preferred form shown in the drawing, two side ports are provided. However, it is contemplated that 1-6 side ports of varying sizes may be utilized in the practice of this invention.

As heretofore mentioned, side ports in the small catheters to which this invention is directed cannot be provided by mechanical means such as skiving which are employed to make holes in larger cannulas, e.g. epidural catheters. Accordingly, an essential part of the present invention is to provide a way to make side ports of the foregoing general description in a microbore catheter. While the initial concept of the present invention was to utilize a laser to provide the side ports, initial efforts using a laser beam were unsuccessful.

Apart from the size restrictions, there were additional requirements that the holes provided should extend through only one wall of the catheter and should not result in cratering or burring which could be detrimental to the contemplated usage. If cratering is external, it will increase the OD and may prevent the catheter from passing through the needle; while internal cratering can reduce the flow rate. Although burring is of lesser concern than cratering, it is still to be avoided because the burrs or small pieces of the catheter tubing can come off within the patient, e.g. In the dura mater during insertion or withdrawal and/or in the subarachnoid space.

In the initial efforts to create the side ports 22a, 22b with a laser beam, a carbon dioxide laser was selected. The carbon dioxide laser employed emits radiation in the infrared (IR) range at around 1000 nm and creates holes or voids by vaporizing a material on absorption of the radiation. It possesses a high energy output and is typically used in the industrial setting.

while the holes in the catheter produced by the carbon dioxide layer were of proper size as anticipated, quite unexpectedly it was found that cratering and burring effects occurred surrounding the hole, rendering the catheter so produced impractical for sale for the contemplated primary use for spinal anesthesia.

Accordingly, another solution was required.

it was found that the problem was not with lasers per se but with the particular laser selected. It was believed that the burring was caused because the particular catheter material employed, nylon, did not absorb substantially all of the laser radiation so that sufficient radiation from the carbon dioxide beam was transmitted to cause the burring rather than being absorbed by the material. The cratering was determined to have been caused by the amount of heat emitted by the laser beam, which heat was absorbed by the catheter material.

It was accordingly theorized that a laser beam could indeed be utilized to obtain the desired side ports not previously obtainable in catheters this small in OD by the known mechanical means if the proper laser could be selected. The selected laser beam should be characterized as being one: (1) whose emitted radiation is in a wavelength such that little or no radiation is transmitted through the target material so as to cause objectionable burring; and (2) does not emit enough heat to cause cratering by heat emitted by the laser being absorbed by the catheter materials, causing it to melt rather than being vaporized.

In the foregoing discussion it will be appreciated that one cannot state unequivocally that no radiation is transmitted, nor can one say that no heat from the laser is absorbed by the catheter material. What one can say is that if any radiation is transmitted or heat absorbed it is insignificant as not adversely affecting the desired physical characteristics, e.g. size, shape, etc. of the hole so produced. In this sense, the selected laser can be characterized as being innocuous in that it does not cause any physical properties to the area surrounding the port which would be regarded by an anesthesiologist or other person skilled in the art as deleterious for use in administering spinal anesthesia.

With this theoretical consideration in mind, it was concluded that if Applicants were correct, what was in fact needed, at least for the nylon catheter employed, was a laser beam of a shorter wavelength and specifically one whose wavelength was sufficiently small that no detrimental heat is emitted.

Excimer lasers meet that description. Excimer lasers emit in the ultraviolet (UV) range and are sometimes referred to as "cold lasers" because they do not create thermal warming, as other lasers do, that can cause severe damage to surrounding material. For this reason they have previously found use in medical procedures such as laser angioplasty where plaque causing blockage of an artery is vaporized with the laser without harm to the fragile artery tissue. Since harmful heating of the area peripheral to the area to be vaporized would be obviated, it was then postulated that the Excimer laser would solve the task to which this application is directed.

it is known that Excimer laser energy exhibits a wavelength in the UV ranging from 40–400 nanometers (nm). Excimer laser energy can be provided, for example, by a laser medium such as argon-chloride having a wavelength of 193 nm; krypton-chloride (222 nm); krypton-fluoride (240 nm) or xenon-chloride (308 nm). The output energy from this type of laser appears in short bursts or pulses that can last for 10–85 nanoseconds and have a high peak energy. Although the destruction mechanism involving this form of energy may not be completely understood, it has been reported in the literature that one pulse of the Excimer laser produces an incision which destroys the target area without accompanying thermal injury to the surrounding area. This result is thought to be due to either or both of the following phenomena: (1) the delivery of the short duration, high energy pulses may vaporize the material so rapidly that heat transfer to the non-irradiated adjacent tissue is minimal; and/or (2) UV photons absorbed in the organic material might disrupt molecular bonds to remove target material photochemically rather than by thermal mechanisms.

Having theorized that an Excimer laser could solve the task of providing the desired side ports, the initial effort was made with a 308 nm Excimer. The hole was produced in about 75 seconds. Holes provided by this Excimer were characterized as being generally cone-shaped with yellow edges. While satisfactory from the performance standpoint, they were concluded to be unacceptable from the marketing standpoint.

Since it was thought that this might be obviated by increasing absorption of the laser beam still further and, moreover, that production time should be decreased, it was next decided to employ a 193 nm Excimer. The desired generally circular holes (no discoloration, burring or cratering) was produced in only three seconds.

While the foregoing test results were performed with a nylon catheter it is believed that the 193 nm Excimer may be equally applicable for providing the side ports in other catheter materials as well. In any case, in the light of the foregoing discussion the selection of the appropriate laser for the particular catheter material employed will involve routine experimentation readily within the expected knowledge of the skilled worker.

while in the foregoing discussion reference has been made to so-called "open tip" catheters having an opening at the tip or terminal end of the lumen along with one or more side ports, the invention also contemplates so-called "bullet" or "closed tip" catheters in which the only openings are the side ports.

From the foregoing discussion it will be seen that the present invention makes it possible to obtain better distribution of drug in the subarachnoid space, e.g. providing a wider spread of drug over the lumbosacral curve.

Since various changes may be made without departing from the scope of the invention herein contemplated, it is to be understood that the foregoing description and accompanying drawing are to be taken as being illustrative and not in a limiting sense.

What is claimed is:

1. The method of making a microbore spinal catheter comprising the steps of:

(1) forming a catheter comprising an elongated flexible wall material having opposed distal and proximal ends and having a single lumen extending between the ends and terminating with an opening at its distal end, the catheter having an outer diameter no greater than about 0.022 inch; and (2) thereafter forming at the distal end proximal to the distal end opening at least one sideport characterized as being spherical and substantially free of any burring or cratering by contacting the catheter wall material with a laser beam selected with respect to the catheter wall material so that:

(a) the radiation emitted by the laser is in a wavelength such that little or no radiation is transmitted through the target catheter wall material; and (b) the radiation does not emit enough heat to cause the target catheter wall material to melt rather than being vaporized.

2. The method as defined in claim 1 wherein the laser is a cold laser emitting in the ultraviolet range.

3. The method as defined in claim 1 wherein the laser is an Excimer laser exhibiting a wavelength of on the order of 193 nm.

* * * * *